United States Patent [19]
Uchiro et al.

[11] Patent Number: 5,986,143
[45] Date of Patent: *Nov. 16, 1999

[54] METHOD OF PRODUCING BIS(4-ALKYLTHIOPHENYL) DISULFIDES

[75] Inventors: Hiromi Uchiro, Akagishitamachi; Norio Kawabe, Gujisawa; Kouichi Tsuruta; Teiji Kawano, both of Kamakura, all of Japan

[73] Assignee: Toray Industries, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/700,507

[22] PCT Filed: Dec. 22, 1995

[86] PCT No.: PCT/JP95/02645

§ 371 Date: Aug. 22, 1996

§ 102(e) Date: Aug. 22, 1996

[87] PCT Pub. No.: WO96/19448

PCT Pub. Date: Jun. 27, 1996

[30] Foreign Application Priority Data

Dec. 22, 1994 [JP] Japan .................................. 6-320777

[51] Int. Cl.$^6$ ................................................. C07C 321/00
[52] U.S. Cl. ................................................. 568/25; 568/26
[58] Field of Search ......................................... 568/25, 26

[56] References Cited

PUBLICATIONS

Feher, Z. Naturforschg B , "Uber den nucleophilen Abbau von Aryltrisulfanen mit Triphenylphosphin", pp. 1030–1033, Feb. 1968.

Schuler, Spectra, Ionization Constants, and Rates of Oxidation of 1,4–Dimercaptobenzene and Properties of the p–Mercaptohenylthiyl Anion Radicals, vol. 97, pp. 5611–5617, Apr. 1993.

Chemical Abstracts CA:85:62748, Abstr of "Synthesis of phenylene–1–2–,–1,3–,and–1,4—dithiols and related compounds". Rodionov, 1974.

Chemical Sources p. 775, 1994.

March, Advanced Organic Chemistry, 1968.

*Primary Examiner*—Gary Geist
*Assistant Examiner*—Jean F Vollano
*Attorney, Agent, or Firm*—Birch, Stewart, Kolasch & Birch, LLP

[57] ABSTRACT

The present invention relates to a method of producing bis(4-alkylthiophenyl) disulfides characterized by (a) reducing directly a 4-alkylthiobenzenesulfonyl chloride, or (b) oxidizing a 4-alkylthiobenzenethiol obtained by reducing a 4-alkylthiobenzenesulfonyl chloride. The present invention is capable of producing the compound below useful as an intermediate of pharmaceuticals.

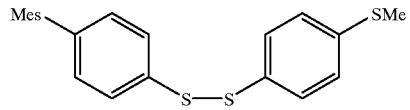

13 Claims, No Drawings

METHOD OF PRODUCING BIS(4-ALKYLTHIOPHENYL) DISULFIDES

This application is the national phase of PCT/JP95/02645 filed Dec. 22, 1995.

TECHNICAL FIELD

The present invention relates to a novel method of producing bis(4-alkylthiophenyl) disulfides useful as intermediates in synthesis of pharmaceutical products and organic industrial products on an industrial scale.

BACKGROUND ART

The inventors have already disclosed in Publication No. WO93/05052 that a series of compounds having alkylthiophenyl groups have various useful pharmacological functions as pharmaceuticals. Alkylthiophenyl groups are generally introduced into those compounds by reacting bis(alkylthiophenyl) sulfides with various nucleophilic reagents.

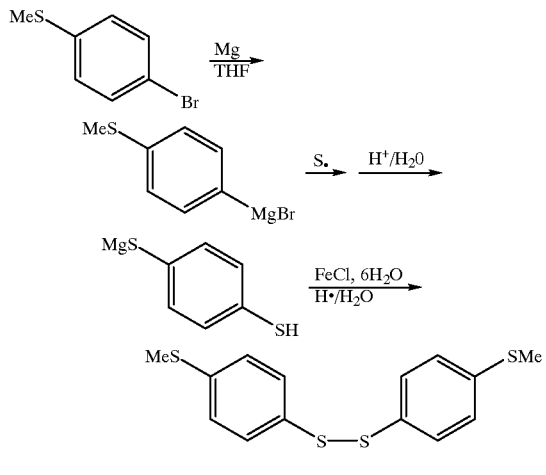

The above publication discloses a method according to the above formulae for synthesizing bis(4-alkylthiophenyl) disulfides among disulfides which are used for the above-described purposes. However, such a method of synthesizing disulfides through a Grignard reaction has the drawback that it is difficult to carry out the method on an industrial scale.

Another method of synthesizing bis(4-alkylthiophenyl) disulfides is disclosed in Synth. Commun., 5(3), 173(1975) in which thioanisole is reacted with disulfur dichloride in the presence of silica gel to obtain bis(4-methylthiophenyl) disulfide. However, this method produces a large amount of bis(4-methylthiophenyl) sulfide as a by-product which cannot be easily removed from the disulfide, and it is difficult to obtain high-purity disulfides. Therefore, this method cannot be used for synthesizing disulfides which are raw materials for the above pharmaceutical products.

A method which is capable of producing high-purity bis(4-alkylthiophenyl) disulfides useful as intermediates in synthesis of pharmaceutical products and organic industrial products on an industrial scale has not been known yet. There is thus strong demand for a novel useful production method.

A method of obtaining 4-alkylthiobenzenethiols from alkyl phenyl sulfides through 4-alkylthiobenzenesulfonyl chlorides is also disclosed in Coltect. Czech. Chem. Commun., 29, 2161(1964)., 39, 3338(974)., 47, 1382(1982). However, this method employs reaction using 5 equivalents of chlorosulfuric acid. In the reaction, therefore, excess chlorosulfuric acid must be decomposed by water after completion of reaction. However, this treatment has the drawback that irritant gases and heat are evolved, and a large amount of waste liquid containing acids is produced.

An object of the present invention is to provide an industrial method of producing bis(4-alkylthiophenyl) disulfides useful as intermediates in synthesis of pharmaceutical products and organic industrial products.

DISCLOSURE OF THE INVENTION

The present invention has the following construction. The present invention relates to a method of producing bis(4-alkylthiophenyl) disulfides comprising (a) directly reducing 4-alkylthiobenzenesulfonyl chlorides or (b) reducing 4-alkylthiobenzenesulfonyl chlorides, and then oxidizing the resultant 4-alkylthiobenzenethiols.

BEST MODE FOR CARRYING OUT THE INVENTION

The method of producing bis(4-alkylthiophenyl) disulfides is represented by the following formulae:

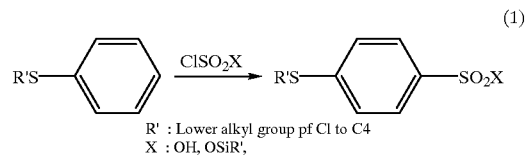

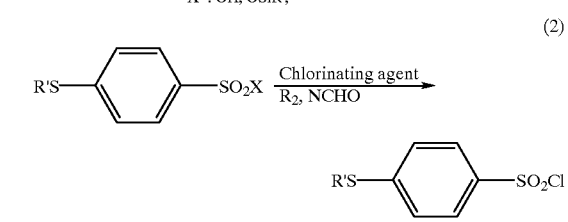

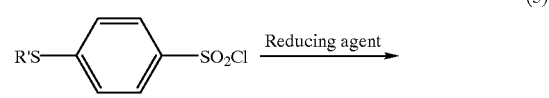

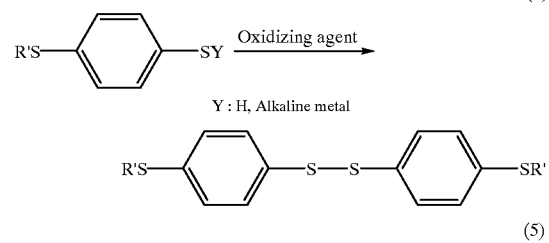

-continued

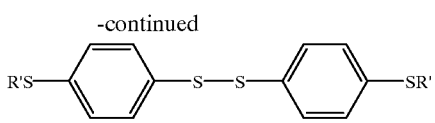

Each step of the reactions is described in detail below.

(1) Sulfonation or silyl sulfonation of alkyl phenyl sulfide

An alkyl phenyl sulfide used in the present invention preferably has a lower alkyl group having 1 to 4 carbon atoms, and methyl phenyl sulfide (thioanisole), ethyl phenyl sulfide, n-propyl phenyl sulfide, and isopropyl phenyl sulfide are particularly preferable.

The amount of chlorosulfuric acid used for sulfonating an alkyl phenyl sulfide must be 1 to 1.5 equivalents to alkyl phenyl sulfide. The object can satisfactorily be achieved by using chlorosulfuric acid in an excess amount of 1.05 to 1.1 equivalents. A suitable reaction solvent is an aliphatic halogenated hydrocarbon having 1 to 3 carbon atoms. Particularly, dichloromethane and 1,2-dichloroethane are preferable. The reaction temperature is preferably 40° C. or lower, more preferably within the range of −10° C. to 15° C.

A preferable silyl sulfonating agent used for silyl sulfonating of an alkyl phenyl sulfide is trialkylsilyl chlorosulfonate. Trialkylsilyl chlorosulfonate preferably has a lower alkyl group (indicated by $R^1$ in formula (1) in the chart of all steps) having 1 to 4 carbon atoms. Examples of such trialkylsilyl chlorosulfonates include trimethylsilyl chlorosulfonate and triethylsilyl chlorosulfonate. Of these compounds, trimethylsilyl chlorosulfonate is economically preferable. Such a silyl sulfonating agent may be prepared separately, or prepared from chlorosulfuric acid and chlorosilane in an aliphatic halogenated hydrocarbon such as dichloromethane or 1,2-dichloroethane and used for silyl sulfonation without being isolated. The amount of the silyl sulfonating agent used is preferably 1 to 1.5 equivalents to alkyl phenyl sulfide from the economical viewpoint. The silyl sulfonation can sufficiently be achieved by using the silyl sulfonating agent in a slightly excess amount of 1.0 to 1.1 equivalents. In preparation of the silyl sulfonating agent, the reaction temperature is preferably 100° C. or lower, more preferably within the range of room temperature to 70° C. The reaction temperature of silyl sulfonation is preferably 40° C. or lower, more preferably within the range of −10° C. to 15° C.

(2) Chlorination of sulfonic acid and silyl sulfonate

The 4-alkylthiobenzenesulfonic acid (a mixture with a small amount of 4-alkylthiobenzenesulfonyl chloride) or silyl 4-alkylthiobenzenesulfonate (a mixture with 4-alkylthiobenzenesulfonic acid) obtained as described above can be converted into 4-alkylthiobenzenesulfonyl chloride without being isolated from the reaction solution of sulfonation or silyl sulfonation. This reaction is preferably effected in the presence of N,N-dialkylamide. N,N-dialkylamide preferably has a lower alkyl group (indicated by $R^2$ in formula (2) in the chart of all steps) having 1 to 4 carbon atoms. For example, dimethylformamide or dimethylacetamide is preferably present, and dimethylformamide is particularly preferable. The amount of the dialkylamide used is preferably 0.05 to 3 equivalents, more preferably 1 to 1.2 equivalents, to alkyl phenyl sulfide used in sulfonation or silyl sulfonation. Examples of chlorinating agents include thionyl chloride, phosphorus pentachloride, phosphorus trichloride and phosphorus oxychloride. Of these compounds, thionyl chloride is preferably used from the economical viewpoint. The amount of the chlorinating agent used is preferably 1 to 2 equivalents, more preferably 1 to 1.2 equivalents, to the alkyl phenyl sulfide used in sulfonation or silyl sulfonation.

(3) Reduction of sulfonyl chloride to thiol

The thus-obtained 4-alkyl thiobenzenesulfonyl chloride can be reduced to 4-alkylthiobenzenethiol by using various reducing agents. This reaction can be effected in the reaction solution without isolation of sulfonyl chloride prepared in the previous step, or in a solution of an aromatic hydrocarbon such as toluene or xylene which contains the sulfonyl chloride is obtained from by distilling off the solvent of the reaction solution. As the reducing agent, for example, a combination of a metal such as zinc or tin, and a mineral acid such as sulfuric acid or hydrochloric acid; and a combination of phosphorus and hydroiodic acid can be used. However, a combination of zinc and hydrochloric acid is economically preferable. The amount of the zinc used is 3 to 10 equivalents, more preferably 4 to 5 equivalents, to the alkyl phenyl sulfide used in sulfonation or silyl sulfonation. The amount of the hydrochloric acid used is preferably 4.5 to 20 equivalents, more preferably 6 to 10 equivalents. The coexistence with a small amount of lead or bismuth and a salt thereof can decrease coloring of the resultant 4-alkylthiobenzenethiol. The amount of the lead used is preferably 0.0005 to 0.01 equivalent to zinc. The reaction temperature is preferably 100° C. or lower, more preferably within the range of room temperature to 80° C.

(4) Oxidation of thiol to disulfide

The thus-obtained 4-alkylthiobenzenethiol can be converted to bis(4-alkylthiophenyl) disulfide by oxidation. Examples of oxidizing agents which can be used include hydrogen peroxide, potassium ferricyanide, dimethylsulfoxide, iron (III) chloride, and the like. Of these agents, hydrogen peroxide is preferably used from the economical viewpoint. The amount of the hydrogen peroxide used is preferably 0.5 to 3 equivalents, more preferably 0.5 to 1 equivalent, to the 4-alkylthiobenzenethiol. To obtain bis(4-alkylthiophenyl) disulfide of higher purity, the 4-alkylthiobenzenethiol obtained by reduction is extracted as an alkali metal salt with an aqueous solution of sodium hydroxide or potassium hydroxide, and then oxidized in the extract solution The reaction temperature is preferably 40° C. or lower, more preferably within the range of 0° C. to 40° C.

The method of the present invention is capable of industrially producing bis(4-alkylthiophenyl) disulfides of high purity with high productivity by using inexpensive reaction reagents. When the same solvent is used in the respective reactions, the product can be obtained without isolation of the intermediates. It is also possible to significantly improve environmental adverse effects of the by-products such as irritant gases and a strongly acidic waste liquid which are problems of a conventional method.

(5) Reduction of sulfonyl chloride to disulfide

The 4-alkylthiobenzenesulfonyl chloride obtained by the reaction described above in (2) can be converted directly into bis(4-alkylthiophenyl) disulfide by reduction with trichlorosilane and trialkylamine. This reaction can be effected in the reaction solution without isolation of sulfonyl chloride prepared in the previous step, or in a solution of an aromatic hydrocarbon such as benzene, toluene or xylene, which contains the sulfonyl chloride obtained from the reaction solution by distilling off the solvent therefrom. Examples of reducing agents which can be used in the reaction include combinations of trichlorosilane and trialkylamines having 1 to 4 carbon atoms, such as dimethylethylamine, diethylmethylamine, dimethylisopropylamine, triethylamine, dimethylbutylamine, diisopropylethylamine, tripropylamine, methyldibutylamine, tributylamine, triisobutylamine, and the like. However, a combination of trichlorosilane and tripropylamine or triethylamine is economically preferable. The amount of the trichlorosilane used is preferably 2 to 10 equivalents, most preferably 3 to 5 equivalents. The amount of the trialkylamine used is preferably 1 to 5 equivalents, most preferably 1.5 to 3 equivalents. The reaction temperature is preferably 0 to 80° C., more preferably within the range of 20 to 40° C.

As described above, the inventors found that 4-alkylthiobenzenesulfonyl chlorides are reduced with trichlorsilane and a trialkylamine to directly obtain bis(4-alkylthiophenyl) disulfides with high yield and high purity.

It was also found that bis(4-alkylthiophenyl) disulfides can also be obtained with high yield and high purity by the simple operation comprising reduction with a reducing agent selected from combinations of zinc and mineral acids and combination of phosphorus and hydroiodic acid to produce a 4-alkylthiobenzenethiol, and oxidation of an alkali extract solution of the thus-produced 4-alkylthiobenzenethiol with an oxidizing agent selected from hydrogen peroxide, potassium ferricyanide, and the like.

As a result of extensive research for developing a synthetic method which can eliminate water treatment and an isolation operation after reaction for obtaining 4-alkylthiobenzenesulfonyl chlorides from alkyl phenyl sulfides, it was found that an alkyl phenyl sulfide is reacted with chlorosulfuric acid in an excess amount of 1 to 1.5 equivalents to obtain 4-alkylthiobenzenesulfonic acid (a mixture with a small amount of 4-alkylthiobenzenesulfonyl chloride), and that the mixture is reacted with a chlorinating agent such as thionyl chloride in the presence of N,N-dialkylamide, e.g., dimethylformamide, to obtain a 4-alkylthiobenzenesulfonyl chloride with high yield. This method has no need for the above water treatment after completion of reaction because chlorosulfuric acid does not remain in the reaction solution. This enables realization of an industrial synthetic process for producing bis(4-alkylthiophenyl) disulfides with minimum amounts of irritant gases and strongly acidic waste liquid.

It was further found that, when an alkyl phenyl sulfide is reacted with a sulfonating agent such as trimethylsilyl chlorosulfonate in place of chlorosulfuric acid, a mixture of 4-alkylthiobenzenesulfuric acid and silyl 4-alkylthiobenzenesulfonate is obtained, and the thus-obtained mixture is reacted with a chlorinating agent in the presence of dimethylformamide by the same method as described above to form 4-alkylthiobenzenesulfonyl chloride, followed by reduction and oxidation to obtain a bis(4-alkylthiophenyl) disulfide with higher yield than the above-described method employing sulfonation.

EXAMPLES

Although the present invention is described in detail below with reference to examples, the present invention is not limited to these examples.

Example 1

Production of 4-methylthiobenzenesulfonyl chloride using sulfonating agent

A dichloromethane (600 ml) solution of 124.2 g (1.00 mol) of thioanisole was cooled to −10° C. 122.4 g (1.05 mol) of chlorosulfuric acid was added dropwise to the solution under stirring so as not to raise the reaction temperature over 0° C. After the reaction mixture was further stirred at 0° C. for 1 hour, the temperature was raised to room temperature, and then the mixture was stirred for 2 hours. 73.1 g (1.00 mol) of dimethylformamide and 124.92 g (1.05 mol) of thionyl chloride were added to the mixture, followed by heating under reflux for 12 hours. The thus-obtained reaction solution was used in the following reaction without any other treatment.

The reaction solution was sampled, and the solvent was distilled off to obtain the target compound.

m. p. 44–45° C.

$^1$H-NMR (CDCl$_3$), δ[ppm]: 2.57 (s, 3H), 7.20–7.50 (m, 4H), 7.75–8.05 (m, 2H)

Example 2

Production of 4-methylthiobenzenethiol (1)

886.9 g (9.00 mol) of concentrated hydrochloric acid (37%) was added to a dichloromethane solution of the 4-methylthiobenzenesulfonyl chloride obtained in Example 1, and the mixture was cooled to 0° C. After 0.27 g (0.001 mol) of lead was added to the mixture, 326.9 g (5.00 mol) of zinc (powder) was gradually added to the mixture at a rate which allowed continuous reflux by reaction heat. After the addition of zinc, the mixture was further stirred at room temperature for 2 hours, and then a solid of the mixture was filtered off. The organic layer of the filtrate was separated, and the aqueous layer was extracted with dichloromethane (200 ml). The organic layer was combined with the extract, and washed with 2N hydrochloric acid (300 ml) and ion-exchanged water (300 ml), followed by three times of extraction with an 2N aqueous sodium hydroxide solution (300 ml). The aqueous extract layer was washed with n-hexane (300 ml), and then filtered through a glass fiber filter to obtain an alkali extract solution of the target compound. In production of bis(4-methylthiophenyl) disulfide, the thus-obtained extract solution was used in reaction of the following step without any other treatment. However, the target compound was obtained by the following operation.

The alkali extract solution obtained by the above method was cooled to 0° C., and the pH of the solution was adjusted to 1 by gradually adding 6N hydrochloric acid under vigorous stirring. After toluene (500 ml) was added to the resultant solution, an organic layer was separated, and an aqueous layer was extracted two times with toluene (250 ml). The organic layer was washed with water (300 ml) and aqueous saturated sodium chloride solution (300 ml), and then dried over anhydrous magnesium sulfate. After drying, the solvent was distilled off to give 137.5 g of the target compound as a colorless oil. The purity of this compound by HPLC analysis was 99%, and the total yield based on the thioanisole was 83%.

b. p. 120° C./10 mmHg $^1$H-NMR (CDCl$_3$), δ[ppm]: 2.44 (s, 3H), 3.41 (s, 1H), 7.03–7.29 (m, 4H)

IR (KBr), [cm$^{-1}$] 2920, 2562, 1479, 1435, 1392, 1321, 1112, 1091, 1013, 969, 806

MS (EI), m/z 156

Elemental analysis (as C$_7$H$_8$S$_2$) Calculated value (%) C: 53.80 H: 5.17 Measured value (%) C: 53.84 H: 5.22

Example 3

Production of 4-methylthiobenzenethiol (2)

Reaction was effected by the same procedure as in Example 2 except that lead was not added. In this example, 136.8 g of the target compound was obtained in the total yield of 88% based on the thioanisole, the purity of the compound by HPLC analysis being 99%. The product was slightly yellow in color.

Example 4
Production of 4-methylthiobenzenethiol (3)

Reaction was effected by the same procedure as in Example 2 except that dicloromethane was distilled off before reaction, and the residue was dissolved in toluene (550 ml). In this example, 139.0 g of the target compound was obtained in the total yield of 89% based on the thioanisole, the purity of the compound by HPLC an a lysis being 99%.

Example 5
Production of bis(4-methylthiophenyl) disulfide (1)

The alkali extract solution of 4-methylthiobenzenethiol obtained in Example 2 was cooled to 0° C., and 62.3 g (0.55 mol) of 30% hydrogen peroxide was slowly added dropwise to the solution under vigorous stirring. After the resulting reaction mixture was stirred at 0° C. for 1 hour, and at 40° C. for 2 hours, the mixture was allowed to stand at room temperature for 1 hour. Toluene (700 ml) was added to the mixture, and the whole solid was dissolved by heating to 40° C. An organic layer was then separated, and an aqueous layer was extracted with toluene (200 ml). The combined organic layer was washed with water (300 ml) and saturated sodium chloride solution (300 ml), followed by drying over anhydrous magnesium sulfate. After drying, the solvent was distilled off to give crystalline residue. The crystal was recrystallized from ethyl acetate/n-hexane to obtain 124.9 g of the target compound as a pale yellow crystal. The purity of the compound by HPLC analysis was 99% or more, and the total yield based on the thioanisole was 80%.

m. p. 84–85° C.

$^1$H-NMR (CDCl$_3$), δ[ppm]: 2.45 (s, 6H), 7.05–7.25 (m, 4H), 7.30–7.50 (m, 4H)

IR (KBr), [cm$^{-1}$] 1475, 1433, 1388, 1098, 1009, 301, 491, 480

MS (EI), m/z 310

Elemental analysis (as C$_{14}$H$_{14}$S4$_2$) Calculated value (%) C: 54.15 H: 4.55 Measured value (%) C: 54.26 H: 4.47

Example 6
Production of bis(4-methylthiophenyl) disulfide (2)

An aqueous solution (1500 ml) of 329.25 g (1.0 mol) of potassium ferricyanide was gradually added to the alkali extract solution of 4-methylthiobenzenethiol obtained by the procedure of Example 2 under vigorous stirring at room temperature. The resultant mixture was stirred at room temperature for 30 minutes, and then allowed to stand for 1 hour. The solid was filtered off, and then washed with water (500 ml) and cool methanol (100 ml) to obtain the target compound as a crude product. After this crude product was dissolved in toluene (700 ml), the resulting solution was washed with water (300 ml) and saturated sodium chloride solution (300 ml), and then dried over anhydrous magnesium sulfate. After the solvent was distilled off, the obtained crystal was recrystallized from ethyl acetate/n-hexane to obtain 122.9 g of the target compound as a pale yellow crystal. The purity of the product by HPLC analysis was 98% or more, and the total yield based on thioanisole was 79%.

m. p. 84–85° C.

Example 7
Production of 4-methylthiobenzenethiol (4)

From a dichloromethane solution of 4-methylthiobenzenesulfonyl chloride obtained by the same procedure as Example 1 the solvent was distilled off, and the resulting residue was then dissolved in toluene (500 ml). 61.94 g (2.00 mol) of red phosphorus and 336.61 g (1.50 mol) of hydroiodic acid (57% aqueous solution) were added to the solution, followed by heating under reflux for 3 hours. After the resultant mixture was cooled to room temperature, insoluble solid was filtered off, an organic layer was separated, and an aqueous layer was extracted with toluene (200 ml). The organic layer was combined and washed with 2N hydrochloric acid (300 ml), followed by three times of extraction with an aqueous 2N sodium hydroxide solution (300 ml). The aqueous alkali extract solution was washed with n-hexane (500 ml) and then filtered through a glass fiber filter to remove insoluble solid.

139.4 g of the target compound was isolated as a colorless oily substance from the filtrate by the same procedure as Example 2. The purity of the product by HPLC analysis was 99%, and the total yield based on thioanisole was 89%.

Example 8
Production of bis(4-methylthiophenyl) disulfide (3)

The filtrate of the alkali extract solution of 4-methylthiobenzenethiol obtained in Example 7 was oxidized by the same procedure as Example 5 to obtain 125.3 g of the target compound as a pale yellow crystal. The purity of the product by HPLC analysis was 99% or more, and the total yield based on thioanisole was 81%.

m. p. 84–85° C.

Example 9
Production of 4-methylthiobenzenesulfonyl chloride using silyl sulfonating agent A dichloromethane (600 ml) solution of 119.5 g (1.10 mol) of trichlorosilane was heated under reflux. 122.4 g (1.05 mol) of chlorosulfuric acid was slowly added dropwise to this solution under vigorous stirring. The resulting mixture was refluxed for 2 hours, and then. cooled to −10° C., and 124.21 g (1.00 mol) of thioanisole was slowly added dropwise to the mixture so as not to raise the reaction temperature over 0° C. After the resultant mixture was further stirred at 0° C. for 1 hour, the temperature of the mixture was raised to room temperature, and then stirred for 2 hours. 73.1 g (1.00 mol) of N,N-dimethylformamide and 124.02 g (1.05 mol) of thionyl chloride were added to the mixture, followed by heating under reflux for 20 hours. The thus-obtained reaction solution was used in the following reaction step without any other treatment.

The reaction solution was sampled, and the solvent was distilled off to confirm the production of the target compound.

m. p. 44–45° C.

Example 10
Production of 4-methylthiobenzenethiol (5)

The dichloromethane solution of 4-methylthiobenzenesulfonyl chloride obtained in Example 9 was reduced by the same procedure as Example 2 to obtain an alkali extract solution of the target compound. In production of a bis(4-alkylthiophenyl) disulfide, the thus-obtained extract solution was used in the following reaction described in Example 11 without any other treatment.

The alkali extract solution obtained by the above method was treated by the same procedure as Example 2 to isolate 145.3 g of the target compound as a colorless oil. The purity of the compound by HPLC analysis was 99% or more, and the total yield based on thioanisole was 93%.

Example 11
Production of bis(4-methylthiophenyl) disulfide (4)

The alkali extract solution of 4-methylthiobenzenethiol obtained in Example 10 was oxidized by the same method as Example 5 to obtain 130.5 g of the target compound as a pale yellow crystal. The purity of the product by HPLC analysis was 99% or more, and the total yield based on thioanisole was 84%.

Example 12
Production of bis(4-methylthiophenyl) disulfide (5)

Dichloromethane was distilled off from the dichloromethane solution of 4-methylthiobenzenesulfonyl chloride obtained in Example 1, and the residue was dissolved in 2.25 l of benzene. 474 g (3.50 mol) of trichlorosilane was added to the resultant solution, and 1.2 l of benzene solution containing 287 g (2.00 mol) of tripropylamine was added to the solution so as not to raise the reaction temperature over 40° C., followed by reaction at 40° C. for 7 hours. After 1.0 l of water was then gradually added to the reaction mixture, the precipitate was filtered off, an organic layer was separated, and an aqueous layer was extracted two times with toluene 500 ml. The organic layer was combined, washed with 500 ml of water, and dried over anhydrous magnesium sulfate. The solvent was then distilled off to obtain the target compound as a crude product. The crude product was recrystallized from ethyl acetate/n-hexane to obtain 121 g of the target compound as a pale yellow crystal. The purity of the product by HPLC analysis was 99%, and the total yield based on thioanisole was 78%.

Example 13
Production of bis(4-methylthiophenyl) disulfide (6)

Dichloromethane was distilled off from the dichloromethane solution of 4-methylthiobenzenesulfonyl chloride obtained in Example 1, and the residue was dissolved in 1.0 l of toluene. 474 g (3.50 mol) of trichlorosilane was added to the resultant solution, and 2.5 l of toluene solution of 253 g (2.50 mol) of triethylamine was added dropwise to the solution so as not to raise the reaction temperature over 30° C., followed by reaction at 30° C. for 4 hours. After 1.0 l of water was gradually added to the reaction solution, the precipitate was filtered off, and an organic layer was separated. An aqueous layer was extracted two times with 500 ml of toluene, and the extract was combined with organic layer. The thus-obtained mixture was washed with 500 ml of water and dried over anhydrous magnesium sulfate, and the solvent was distilled off to obtain the target compound as a crude product. The crude product was recrystallized from ethyl acetate/n-hexane to obtain 105 g of the target compound as a pale yellow crystal. The purity of the product by HPLC analysis was 99%, and the total yield based on thioanisole was 68%.

Example 14
Production of bis(4-methylthiophenyl) disulfide (7)

Dichloromethane was distilled off from the dichloromethane solution of 4-methylthiobenzenesulfonyl chloride obtained in Example 1, and the residue was dissolved in 1.0 l of toluene. 253 g (2.50 mol) of triethylamine was added to the resultant solution, and 2.0 l of toluene solution of 542 g (4.00 mol) of trichlorosilane was added dropwise to the solution so as not to raise the reaction temperature over 30° C., followed by reaction at 30° C. for 2 hours. After 1.0 l of water was gradually added to the reaction solution, the precipitate was filtered off, and an organic layer was separated. An aqueous layer was extracted two times with 500 ml of toluene, and the extract was combined with the organic layer. The thus-obtained mixture was washed with 500 ml of water and dried over anhydrous magnesium sulfate, and the solvent was distilled off to obtain the target compound as a crude product. The crude product was recrystallized from ethyl acetate/n-hexane to obtain 117 g of the target compound as a pale yellow crystal. The purity of the product by HPLC analysis was 99%, and the total yield based on thioanisole was 75%.

INDUSTRIAL APPLICABILITY

The bis(4-alkylthiophenyl) disulfides obtained in the present invention can be used for synthesizing methanediphosphonic acid derivatives which are remedies for metabolic bone diseases such as osteoporosis and diseases such as chronic rheumatism, by the method disclosed in Publication No. WO93/5052, for example, employing the following formulae:

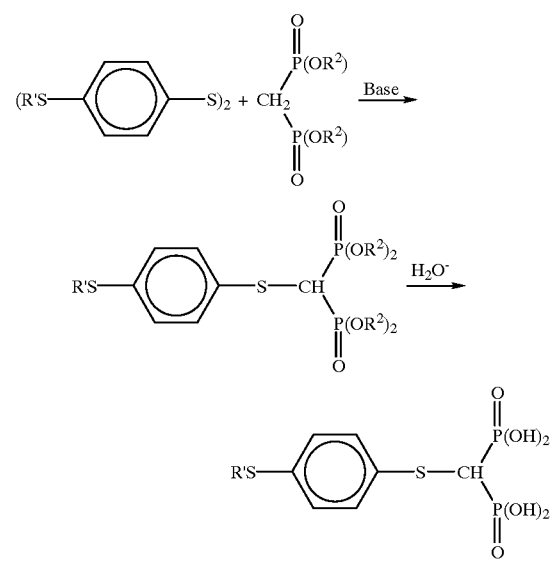

We claim:
1. A method of producing a bis(4-alkylthiophenyl) disulfide, comprising the steps of oxidizing a 4-alkylthiobenzenethiol obtained by reducing a 4-alkylthiobenzenesulfonyl chloride which is obtained by (1) sulfonating the 4-position of an alkyl phenyl sulfide, and (2) chlorinating the resultant 4-alkylthiobenzenesulfonic acid to obtain the desired 4-alkylthiobenzenesulfonyl chloride by using 1.0 to 1.2 equivalents of dimethylformamide and thionyl chloride, said equivalents being based upon the alkylphenyl sulfide.

2. A method of producing a bis 4-alkylthiophenyl disulfide according to claim 1, wherein sulfonation of the 4-position of an alkyl phenyl sulfide is performed by using a sulfonating agent in an amount of 1.0 to 1.5 equivalents to the alkyl phenyl sulfide.

3. A method of producing a bis(4-alkylthiophenyl) disulfide according to claim 1, wherein chlorination of 4-alkylthiobenzenesulfonic acid is performed by using 1.0 to 1.2 equivalents thionyl chloride, said equivalents based upon the alkylphenyl sulfide.

4. A method of producing a bis(4-alkylthiophenyl) disulfide according to claim 1, wherein a 4-alkylthiobenzenesulfonyl chloride is reduced with zinc and a mineral acid to obtain a 4-alkylthiobenzenethiol.

5. A method of producing a bis(4-alkylthiophenyl) disulfide according to claim 4, wherein the 4-alkylthiobenzenesulfonyl chloride is reduced with zinc and a mineral acid in coexistence with at least one of lead, bismuth and salts thereof.

6. A method of producing a bis(4-alkylthiophenyl) disulfide according to claim 1, wherein the 4-alkylthiobenzenethiol is oxidized in an aqueous solution of an alkali metal salt of 4-alkylthiobenzenethiol.

7. A method of producing a bis(4-alkylthiophenyl) disulfide according to claim 6, wherein the aqueous alkali metal salt solution of the 4-alkylthiobenzenethiol is an alkali extract solution obtained from reduction reaction of 4-alkylthiobenzenesulfonyl chloride.

8. A method of producing a bis(4-alkylthiophenyl) disulfide according to claim 1, wherein the 4-alkylthiobenzenethiol is oxidized by using hydrogen peroxide as an oxidant.

9. A method for producing a bis(4-alkylthiophenyl) disulfide, comprising the steps of (1) sulfonating the 4-position of an alkyl phenyl sulfide using a sulfonating agent, (2) chlorinating the obtained 4-alkylthiobenzenesulfonic acid, (3) reducing the obtained 4-alkylthiobenzenesulfonyl chloride using zinc and a mineral acid in the presence of at least one of lead, bismuth and salts thereof, and (4) oxidizing the obtained 4-alkylthiobenzenethiol.

10. A method for producing a bis(4-alkylthiophenyl) disulfide, comprising the steps of (1) sulfonating the 4-position of an alkyl phenyl sulfide using a sulfonating agent, (2) chlorinating the obtained 4-alkylthiobenzenesulfonic acid, (3) reducing the obtained 4-alkylthiobenzenesulfonyl chloride, (4) alkali-extracting the reduction mixture of the 4-alkylthiobenzenesulfonyl chloride, and (5) oxidizing the obtained 4-alkylthiobenzenethio alkali metal salt aqueous solution by hydrogen peroxide.

11. A method for producing a bis(4-alkylthiophenyl) disulfide by oxidizing a 4-alkylthiobenzenethiol obtained by reducing a 4-alkylthiobenzenesulfonyl chloride comprising the steps, wherein (1) the 4-position of an alkylphenyl sulfide is sulfonated using 1.0 to 1.5 equivalents of a sulfonating agent, (2) the obtained 4-alkylthiobenzenesulfonic acid is chlorinated using 1.0 to 1.2 equivalents of dimethylformamide and 1.0 to 1.2 equivalents of thionyl chloride, both equivalents based upon the alkyl phenyl sulfide, (3) the obtained 4-alkylthiobenzenesulfonyl chloride is reduced using zinc and a mineral acid in the presence of at least one of lead, bismuth and salts thereof, (4) the 4-alkylthiobenzenethiol is obtained by extracting the reduction mixture of the 4-alkylthiobenzenesulfonyl chloride with an aqueous solution of alkali metal, and (5) the obtained alkali metal salt of 4-alkylthiobenzenethiol in the aqueous solution is oxidized by hydrogen peroxide.

12. A method of producing a bis(4-alkylthiophenyl) disulfide comprising (1) sulfonating the 4-position of an alkyl phenyl sulfide; and (2) chlorinating the resultant 4-alkylthiobenzenesulfonic acid to obtain a 4-alkylthiobenzenesulfonyl chloride; said chlorinating being performed by using 1.0 to 1.2 equivalents of dimethylformamide and 1.0 to 1.2 equivalents of thionyl chloride, both equivalents being based upon the alkyl phenyl sulfide; and (3) reducing the obtained 4-alkylthiobenzenesulfonyl chloride of step (2) to obtain a 4-alkylthiobenzenethiol; and (4) subsequently oxidizing the obtained 4-alkylthiobenzenethiol of step 3 to yield the desired bis(4-alkylthiophenyl) disulfide.

13. A method of producing a bis(4-alkylthiophenyl) disulfide according to claim 12, wherein the 4-alkylthiobenzenesulfonyl chloride is reduced with zinc and a mineral acid in coexistence with at least one of lead, bismuth and salts thereof.

* * * * *

UNITED STATES PATENT AND TRADEMARK OFFICE
CERTIFICATE OF CORRECTION

PATENT NO. : 5,986,143
DATED : November 16, 1999
INVENTOR(S) : Uchiro et al.

It is certified that error appears in the above-identified patent and that said Letters Patent is hereby corrected as shown below:

Claim 1, line 10, change "alkylphenyl sulfide" to -- alkyl phenyl sulfide --.

Claim 3, line 5, change "alkylphenyl sulfide" to -- alkyl phenyl sulfide --.

Claim 10, line 9, change "4-alkylthiobenzenethio" to -- 4-alkylthiobenzenethiol --.

Claim 11, line 4, change "alkylphenyl" to -- alkyl phenyl --.

Signed and Sealed this

First Day of May, 2001

Attest:

NICHOLAS P. GODICI

Attesting Officer     Acting Director of the United States Patent and Trademark Office